(12) United States Patent
Nuotio et al.

(10) Patent No.: US 8,197,776 B2
(45) Date of Patent: Jun. 12, 2012

(54) REACTION VESSEL AND METHOD FOR THE HANDLING THEREOF

(75) Inventors: Vesa Nuotio, Vantaa (FI); Juhani Makunen, Vantaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 0 days.

(21) Appl. No.: 12/993,710

(22) PCT Filed: May 27, 2009

(86) PCT No.: PCT/FI2009/050450
§ 371 (c)(1),
(2), (4) Date: Nov. 19, 2010

(87) PCT Pub. No.: WO2009/144380
PCT Pub. Date: Dec. 3, 2009

(65) Prior Publication Data
US 2011/0064543 A1 Mar. 17, 2011

(30) Foreign Application Priority Data
May 28, 2008 (FI) .................................... 20085509

(51) Int. Cl.
*B01L 3/00* (2006.01)
(52) U.S. Cl. ........................................................ 422/559
(58) Field of Classification Search .................... 422/559
See application file for complete search history.

(56) References Cited

U.S. PATENT DOCUMENTS

| 3,759,374 | A | * | 9/1973 | Helger et al. ............... 206/431 |
| 5,096,672 | A | * | 3/1992 | Tervamaki et al. .......... 422/552 |
| 5,110,556 | A | | 5/1992 | Lyman et al. |
| 5,308,584 | A | * | 5/1994 | Vauramo ..................... 422/566 |
| 5,470,536 | A | | 11/1995 | Järvimäki |
| 5,538,493 | A | | 7/1996 | Gerken et al. |
| 5,650,125 | A | * | 7/1997 | Bosanquet ................... 422/548 |
| 5,952,173 | A | * | 9/1999 | Hansmann et al. .......... 435/6.11 |

(Continued)

FOREIGN PATENT DOCUMENTS
EP  0 415 307 A2  3/1991
(Continued)

OTHER PUBLICATIONS

Office Action for U.S. Appl. No. 12/993,710. Office Action mailed on Aug. 5, 2011. 11 pages.*

*Primary Examiner* — Bobby Ramdhanie
(74) *Attorney, Agent, or Firm* — Birch, Stewart, Kolasch & Birch, LLP

(57) ABSTRACT

A cuvette (10) for an automatic analyzing apparatus according to the invention includes at least two positions (20), for each position pair one separating wall (22) connecting the positions (20), and brackets (24), which are at the outermost positions (20) and which guide the cuvette (10) into a curved shape. In a handling method of a cuvette (10) according to the invention a cuvette (10) is transported from its brackets (24) to an incubator (30) and bent into a curved shape. In the method the cuvette (10) is then loaded into an opening (34) of the incubator (30), in which opening (34) it remains by its own spring back factor, until the cuvette (10) is removed from the opening (34) after the analysis.

13 Claims, 3 Drawing Sheets

| U.S. PATENT DOCUMENTS | | | |
|---|---|---|---|
| 6,001,310 A | 12/1999 | Shaffer et al. | |
| 2003/0003591 A1 | 1/2003 | LaCourt et al. | |
| 2003/0087447 A1 | 5/2003 | Blouin et al. | |
| 2005/0249640 A1 | 11/2005 | Kansy et al. | |
| 2008/0031776 A1 | 2/2008 | Sevigny et al. | |

| FOREIGN PATENT DOCUMENTS | | |
|---|---|---|
| EP | 0 597 288 A1 | 5/1994 |
| EP | 0 688 602 A2 | 12/1995 |
| GB | 2 036 364 A | 6/1980 |
| WO | 2006/038345 A2 | 4/2006 |

\* cited by examiner

REACTION VESSEL AND METHOD FOR THE HANDLING THEREOF

CROSS-REFERENCE TO RELATED APPLICATIONS

The present application claims priority under 35 USC 119 to Finish Patent Application No. 20085509 filed on May 28, 2008 and PCT Patent Application No. PCT/FI2009/050450 filed on May 27, 2009 the entire contents of which are hereby incorporated by reference.

BACKGROUND OF THE INVENTION

1. Field of the Invention

The present invention relates to a new type of a reaction vessel, i.e. a cuvette, for usage in automatic analyzers and to a cuvette incubation method. More precisely, the present invention relates to a cuvette and an incubation method according to the preambles of the independent claims.

2. Description of Background Art

As known, disposable and reusable cuvettes have been used in automatic analyzers as individual cuvettes or as sets of cuvettes. Cuvettes are vessels into which a sample to be analyzed and possible other substances to be used in the test are portioned out for the analysis. Reusable cuvettes are cleaned between the analyses, whereas disposable cuvettes are designed to receive only one sample during their life span. The cleaning of the cuvettes between the tests is laborious due to the properties of the cleaning products and to the potentionally dangerous substance to be removed. Thus, especially when performing a large amount of tests, disposable cuvettes are favored, which are delivered to waste treatment after use and it is certain enough that they are clean at least when taken into use.

Disposable cuvettes are known that there are manufactured as a continuous chain of cuvettes, which can be bent about two axes into a spiral shape and which are adapted to be moved, wrapped around the moving orbicular bodies of the analyzer. Likewise, columns of cuvettes are already known, which can be moved from cuvette specific protrusions, between which conveying members, such as toothed belts, are adapted to penetrate. As known, the attachment of the cuvette or the set of cuvettes to a testing apparatus is performed with external shaped connection of the cuvette, such as pin couplings, and such that the receiving means of the testing apparatus comprising flexible separating walls hold the cuvette in place.

However, the prior art has some disadvantages. The cuvettes according to prior art are usually suitable to be used in only one application, whereby they have not been suited to be used in several different types of analyzers and incubators. The known cuvette-incubator-pairs have included a plurality of maneuvers and precision mechanics and, thus, not being particularly robust in structure nor in operation. In addition, said pairs are typically test-oriented, which means that only analyses of a specific test, typically a photometric analysis, is performed in one test sequence. This is why there have been gratuitous delays in receiving patient or sample specific results. Likewise, the abundance of maneuvers has resulted in that the sample-carrying cuvettes being exposed to several contacts, which has worn their outer surfaces. In some cases excess wear has have impaired the optical properties of the clear vessels. The wear and tear is especially intensive when the vessels are being washed, which is disadvantageous only with reusable cuvettes.

SUMMARY AND OBJECTS OF THE INVENTION

An object of an embodiment of the present invention is to solve at least part of the aforementioned problems and to provide an improved cuvette and a handling method thereof.

A cuvette according to the invention comprises two positions, which are connected by a separating wall, and at least one bracket at the outermost positions being able to support the cuvette and yield elastically when pressed inward. The separating walls between the cuvette positions allow for the elastic bending of the cuvette about its vertical axis. More precisely, the cuvette according to the present in invention is characterized by what has been stated in the characterizing portion of the independent apparatus claim.

In a cuvette handling method according to the present invention a cuvette is transported from its brackets to an incubator and it is bent into a curved shape after which the cuvette is loaded into an incubator opening in which it remains by means of its own spring back factor. Hereafter the sample to be analyzed is portioned out into the sample space of the position of the cuvette, it is analyzed while being in the incubator, and the cuvette is finally removed from the incubator opening. More precisely, the handling method according to the present invention is characterized by what has been stated in the characterizing portion of the independent method claim.

Considerable advantages are gained with the aid of the invention. Due to the brackets and elasticity along the vertical axis, the cuvette according to the present invention can advantageously be used in apparatuses that automatically analyze samples. Due to the suitable yielding properties the cuvette may be transported to an incubator and loaded therein without scratching the vulnerable optical surfaces of the cuvette. Likewise, the brackets contribute to bending the cuvette tightly into the exact bow for it to be throughout its length in continuous contact with the walls of the receiving incubator opening. With the aid of the brackets is also easy to place and center the cuvette into the receiving incubator opening.

The loading and ejecting movement of the handling method comprises only one direction and movement, whereby the method is robust and reliable. Due to the yielding properties in relation to the vertical axis of the cuvette, neither excess shaped connections nor precision mechanics is required. For the same reason one type of cuvette can be used in various different incubators resulting in considerable cost savings for the user. In addition to the previously mentioned advantages, the sufficiently long brackets and the separating walls separating the positions of the cuvette according to the present invention guarantee that there is an even temperature distribution during the test sequence in the cuvette. Thus, the heat conducting from one sample space to another does not compromise the accuracy and reliability of the test.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
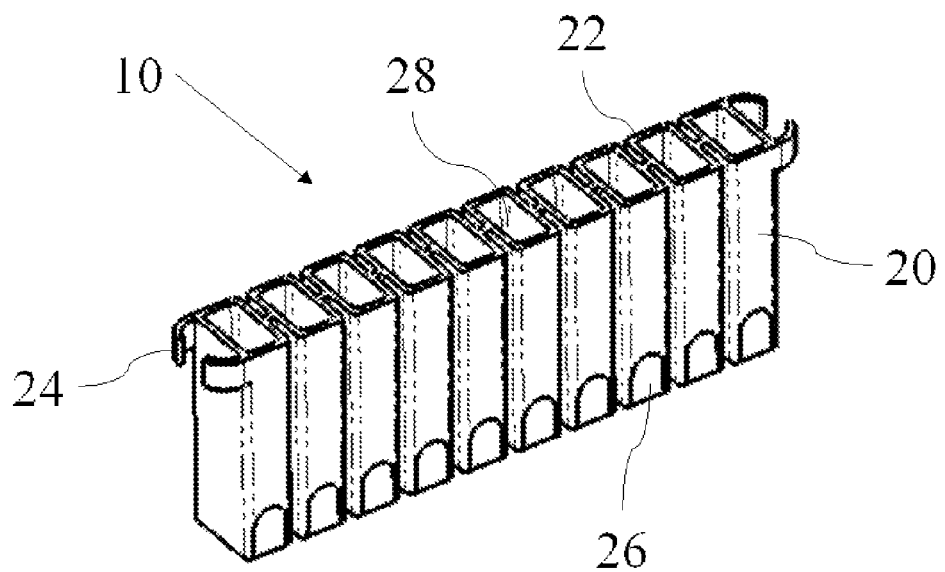
FIG. 1 shows an isometric view of a cuvette with 10 positions.

As illustrated in FIG. 1, the cuvette 10 comprises positions 20, which are in line next to each other. By a cuvette 10 is meant in this context a sample-receiving member with at least one position 20 for receiving the sample and for storage at least during analysis. The position 20 is a tubular vessel wherein a confined sample space 28 for a sample to be analyzed is formed and which is limited by the walls of the vessel. The position 20 has, according to one embodiment, a rounded quadrangular shaped cross-section and is generally shaped such that the sides of the opening of the sample space 28 are considerably shorter than the depth thereof. The sample space 28 can also have another shape. In this context, the direction of the longest side of the sample space 28 of the position 20, i.e. the depth, is called the vertical axis. Correspondingly by a horizontal axis is meant the Cartesian axes orthogonal to the vertical axis.

Figure 2:
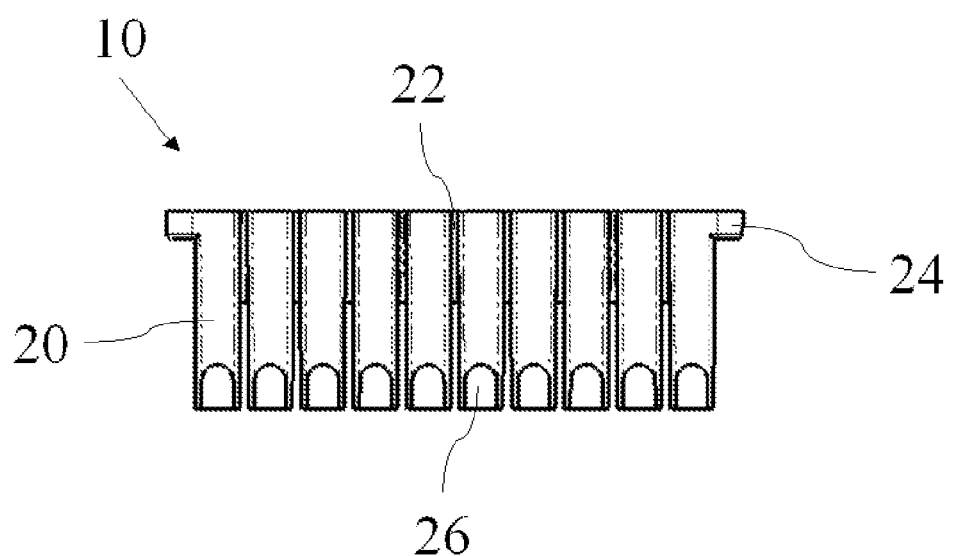
FIG. 2 shows a side view of the cuvette of FIG. 1.

The cuvette 10 has, according to one embodiment of the invention, 10 positions, which are separated from each other by separating walls 22. The separating wall 22 is an isthmus-like connecting part between two positions 20. As illustrated in FIGS. 1 and 2, the separating wall 22 is essentially in the middle of the narrow faces of the parallel positions 20 such that the separating wall 22 extends from the upper edge of the cuvette 10 to about half way of the side face of the positions 20. In other words, the separating wall 22 does not connect the positions 20 over their whole length, but only along their upper half. The basic idea of the separating wall 22 is to be a connecting element, which does not contribute to transfer heat from position to another, but on the contrary isolates the positions 20 from each other. Thus, the heat conducted between the positions 20 remains as minimal as possible, which improves the accuracy of the analysis.

Figure 3:
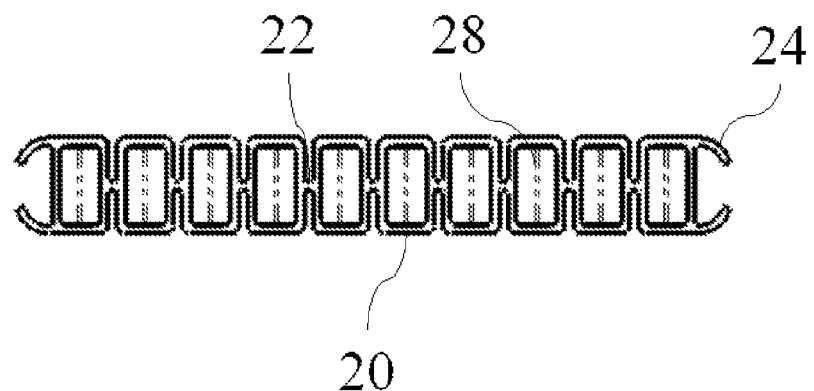
FIG. 3 shows an elevated view of the cuvette of FIG. 1.

One essential feature of the separating wall 22 is its elasticity. As illustrated in FIG. 3, the separating walls 22 are rather thin compared to the walls of positions 20, especially compared to their vertical length. Due to the profile of the separating walls 22 and the elastic material thereof, the cuvette 10 can be bent about its vertical axis, i.e. about the axis directed orthogonally upward from the plane of FIG. 3. By elastic material is in this context meant a material, which is elastic enough to cope with intended deformations it experiences. The material of the cuvette 10 and especially of the separating wall 22 is selected such that the construction may be exposed to bending, whereby the separating walls 22 experience elastic deformation, due to which elasticity the cuvette 10 tends to react against the bending thus tautening itself back to its original position. Thus, the elasticity of separating walls 22 is essential, because the structure must remain elastic also under bending strain for reasons explained later on. Besides elasticity the material must have suitable optical properties at least as positions 20 are concerned. Plastic, especially acryl, is for example a sufficiently elastic and suitable bright material. Alternatively the cuvette 10 may be manufactured of more than one material. In this case, parts requiring yielding properties, such as brackets 24 and separating walls 22, can be made of essentially elastic material, such as polyurethane, and parts requiring optical properties, such as positions 20, can be made of material having good optical properties, such as acryl. Furthermore, upon material selection, it is possible to favor materials that have good optical characteristics. For example, a material can be favored, which is elastic in its application, but of which material made cuvette 10 is not adapted to recover entirely after the bending, but the separating walls 22 of the cuvette 10 would experience partial plastic deformation. Thus, the cuvette 10 would remain slightly bent after use, which would indicate that the product has been used and reuse would be prohibited.

As illustrated in FIGS. 1, 2 and 3, the outermost positions 20 are equipped with brackets 24. According to one embodiment of the invention, the bracket 24 consists of two protrusions, which are considerably shorter in the direction of the vertical axis of the cuvette 10 than the cuvette 10 and which are rather fragile in regard to their wall thickness. The protrusions of the bracket 24 are oriented outward from the upper part of the outer edge of the outermost positions 20 such that the protrusions curve towards each other. By the outer edge of the position 20 is meant the side edge of either of the outermost position 20 not having a separating wall 22. Correspondingly, the direction oriented outward is the horizontal direction oriented from the separating wall 22 toward the outer edge of the position 20.

The brackets 24 are, as the separating walls 22, of elastic material, due to which they too endure elastically the bending about their longest side. The yielding properties of the brackets 24 are the best in the orientation direction of the cuvette 10. Thus, the protrusions of the brackets 24 persist the compression toward the position 20. The elasticity of the brackets 24 is essential, because the structure must remain elastic under compression due to reasons explained later on. It is likewise important that the inward compressed brackets 24 do not bend into contact with the position 20 under compression, but keep a distance between the fixation and the position 20, whereby there is no thermal conduction between its outer edge and the fixation. If there were to occur thermal conduction between the fixation and the outermost positions 20 of the cuvette 10, they would receive more heat than the rest of the positions 20. In such a case, an uneven temperature distribution would be formed into the cuvette 10, which would impair the accuracy of the measurement.

As is apparent from FIGS. 1 and 2, the positions 20 of the cuvette 10 may be equipped with screens 26 suitable for optical analysis. According to one embodiment of the present invention, the screen 26 is a part in the lower end of the position 20, which has been made transparent and which has suitable optical properties for analysis. In addition, the screen 26 must be large enough for the analyzing ray to fit reliably across the position 20 and for the small aligning errors caused by the mechanical parts of the analyzing apparatus not to make the measurement more difficult. It is thus possible to perform analyses based on optical examination such that the sample remains in the sample space 28 of the position 20, whereby the number of maneuvers and sample transfers is small as possible. In order to avoid excess wear and tear of the screen 26, its sensitive surface can be manufactured such that it is slightly deeper than the rest of the face of the position 20. Said cavity provides protection from the majority of scratching contacts, whereby wearing occurring during the packaging phase, for example, is directed toward the side faces of the positions 20 instead of toward the screens 26.

Figure 4:
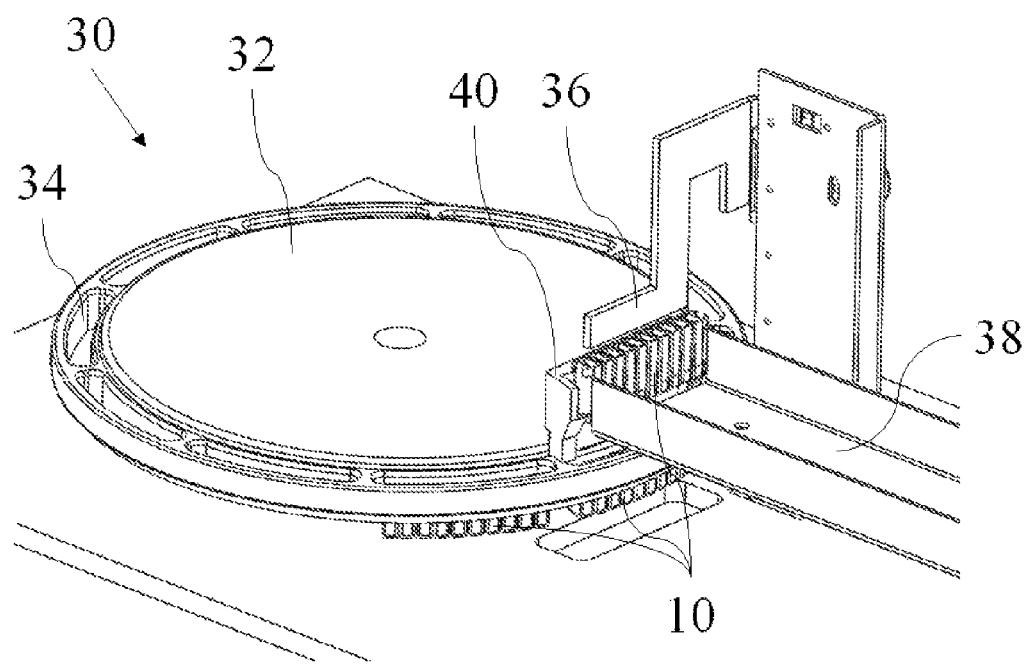
FIG. 4 shows an incubator and a cuvette, which can to be adapted to its orbicular body.

As illustrated in FIG. 4, the cuvette 10 is especially suitable to be used in an automatic incubator 30. According to one preferred embodiment, the incubator 30 comprises a heated disc 32 into the outer perimeter of which openings 34 for receiving the cuvettes 10 have been made. The disc 32 is fitted with a bearing in the middle wherein means for rotation (not shown) are arranged, with the aid of which the disc 32 can be rotated a desired amount in a desired direction. The rotation means can, for example, comprise a servomotor, which has excellent positioning accuracy but which is considerably expensive. The power transmission of the incubator 30 can be arranged with sufficient accuracy by fitting the disc directly on the axle of a cost efficient and sufficiently accurate stepping motor, whereby the transmission has only a necessary amount of moving parts and as few sources of play as possible. The incubator 30 further comprises, in connection with the disc 32, a loading track 38, along which cuvettes 10 are brought to be loaded into the opening 34 of the disc 32. The loading track 38 is in its simplest embodiment a channel having a U-shaped cross-section and whose horizontal edge is essentially as wide as the lower edge of the cuvette 10 and whose vertical edges are essentially lower than the cuvette 10. Thus the cuvette 10 may be transported from its brackets 24 along the loading track 38 such that the brackets 24 of the cuvette 10 are placed on top of the vertical edges of the loading track 38, whereby the lower edges of the positions 20 are at a distance from the bottom of the loading track 38. The gap between the lower edge of the positions 20 and the bottom of the loading track 38 makes it possible for the lower edge of the position 20 not to grind the bottom of the loading track 38 and thus preventing scratching.

Figure 5:
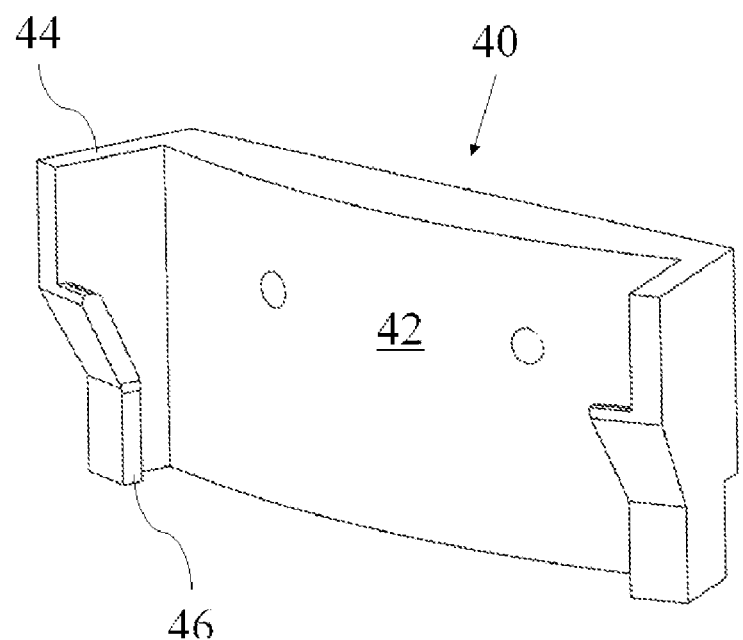
FIG. 5 shows the loading funnel of the incubator of FIG. 4.
Figure 6:
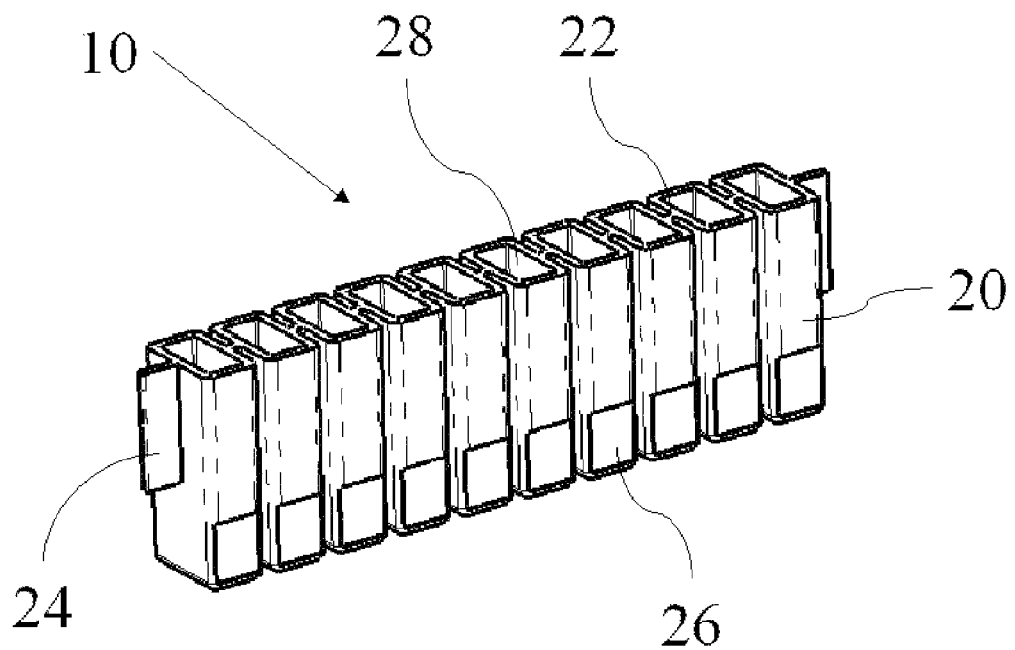
FIG. 6 shows a cuvette according to another embodiment of the present invention equipped with single projection brackets.

To the loading track 38 side of the disc 32 a loading funnel 40 has been fitted, through which cuvettes 10 are loaded into the openings 34 of the disc 32. The loading is performed by using a press 36, the lower edge of which is adapted to press the cuvette 10 into the loading funnel 40, in which it is adapted to acquire a shape allowing it to fit into the opening 34 and to proceed into the opening 34. The curvature of the opening 34 conforms to the curvature of the disc 32. Due to of the elasticity of the cuvette 10, it may be used with various discs 32 and further openings 34 with different curvature radii. As is apparent from FIG. 5, the loading funnel 40 is shaped such that a cuvette 10 passing through it assumes a curved shape able to fit into the opening 34. The cuvette 10 receiving edge 42 of the loading funnel 40 is convex when viewed from the entering direction of the cuvette, whereby a cuvette 10 pressed against it bends into a shape conforming to the perimeter of the disc 32. The curvature of the receiving edge 42 of the loading funnel 40 can be planar, i.e. constant, or it can vary in the horizontal direction, whereby the receiving edge 42 is planar at its upper edge and progressively convex when viewed lower. Thus the cuvette 10 is adapted to bend gradually conforming to the receiving edge 42, whereas the face 42 being evenly curvaceous, the cuvette 10 is adapted to bend immediately to the curve shape desired. The loading funnel 40 is also equipped with brackets 24 with receiving side edges 44, against whose inner edge the brackets 24 are pressed. Thus, the cuvette 10 is in intensive contact with the loading funnel 40 only at the brackets 24, whereby they receive the wear and scratching resulting from bending. Therefore the fragile surfaces of the cuvette 10, such as screens 26 and their surroundings, avoid erosion. Furthermore, the side edges 44 of the loading funnel are equipped with guides 46 securing that the brackets 24 of the cuvette 10 are pressed against the inner faces of the side edges 44. When the cuvette 10 is pressed against the lower edge of the loading funnel 40, its brackets 24 are pressed in and the separating walls 22 are bent, whereby the cuvette 10 is tightly curved against the receiving face 42 of the loading funnel 40 and ready to be loaded equally tightly in to the opening 34 of the disc 32. With the aid of the brackets 24 the cuvette 10 is placed and centers itself automatically into the opening 34 even though the disc 32 should not be in the exactly correct position. The cuvette 10 can certainly have a different construction achieving the qualities described above. For example, a cuvette 10 illustrated in FIG. 7 could be a possible embodiment, but only if it would result in above described qualities. Likewise, the cuvette 10 could also be straight and not adapted to assume a curved shape, whereby the cuvette 10 would be designed to remain in a corresponding straight opening 34 only due to the elastic properties of its brackets.

The path of the press 36 is so long that the upper edge of the cuvette 10 is at a desired height when it is pressed in to the opening 36. Accordingly, the pressing depth of the press 36, which may be programmed to suit the application, determines the vertical alignment. As above, the when loading the cuvette 10 into the opening 34 its brackets 24 receive the most abrasion, which the other surfaces avoid. As the cuvette 10 is in the opening 34 of the incubator 30, the fluid or other substance to be analyzed can be distributed into the sample spaces 28. It is to be noted that the cuvette 10 may be designed for incubators 30 with discs 32 and further openings 34 of various sizes, as described above. Thus, a cuvette 10 of a certain size can be used in various applications, which provides considerably cost savings while the variety of cuvettes is minimal.

The disc 32 is heated for maintaining as favorable analyzing conditions as possible, due to which heat is conducted to positions 20 and further to sample spaces 28 through the side face of the opening 34. With the aid of separating walls 22 the positions 20 are separated from each other not causing temperature distortion with their preheat between adjacent positions 20. An even temperature is further improved by sufficiently prominent brackets 24, which isolate the outer edges of the outer positions 20 of the cuvette 10 from the heated faces of the opening 34.

The analyzing apparatuses have been arranged around the incubator 30 such that there is no need to remove the cuvette 10 from the opening 34 during testing. For example, optical tests may be performed directly through the screen 26 of the position 20. Therefore, the position 20 of the cuvette 10 loaded from the loading track 28 into the opening 34 of the incubator 30 is adapted to receive substances from several manipulators by changing the position of the disc 32. The analyzing procedure can in this case be arranged such that the reagent is portioned out into the sample space 28 of the position 20 by means if a reagent dispenser, which retrieves the substance from a reagent storage. The dispensing of the reagent requires that the disc 32 of the incubator 30 has been rotated into a correct position such that the correct position 20 is in a reagent receiving position. The basic idea of the arrangement is that the sample is moved in the cuvette 10, the position of which is changed by rotating the disc 32 of the incubator, whereby the number of maneuvers and directions is as small as possible. The samples for their part are dispensed in a similar manner by means of a sample dispenser, which retrieves the substance from a sample storage. The reagent and sample can be mixed by rotating the disc 32 into the vicinity of a mixer and by starting the mixer. The contents of the position 20 can be analyzed optically as described above and, for example, with a manipulating analyzer adapted to suck the sample into its test space and to measure its voltage compared to a reference value. The sectioning and programming of the test sequences and maneuvers is previously known.

When the tests performed to all used positions 20 are completed, the cuvette 10 can be ejected from the opening 34 such that the press 36 having performed the loading pushes the cuvette 10 out of the opening 34 into a separate receiving bin or into the waste opening 50 of the incubator 30. Alternatively, the press 36 can load a new cuvette 10 through the loading funnel 40 into the opening 34, whereby the used cuvette 10 is pushed out by the new one into a separate waste bin or into the waste opening 50 of the incubator 30.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A cuvette for an automatic incubator, comprising:
   at least two positions, connected by
   a separating wall, a number of which is totally one less than a number of the at least two positions, and
   brackets,
   wherein the brackets are in outermost positions, and are adapted to guide the cuvette into a curved shape, and
   wherein the brackets further comprise:
   flexible protrusions, which curve outwards and towards each other from upper edges of outer corners of the outermost positions,
   whereby the brackets are adapted to be elastic in a position orientation direction, and to be torsionally rigid in a vertical direction.

2. A cuvette according to claim 1
   wherein the brackets are elastically flexible when pressed in.

3. A cuvette according to claim 2,
   wherein the separating wall connects parallel positions along at most half of a side face of the cuvette to improve an even temperature distribution.

4. A cuvette according to claim 2,
   wherein the separating walls allow the cuvette to bend elastically about a vertical axis.

5. A cuvette according to claim 2,
   wherein the cuvette is made of a material with optical and elastic properties.

6. A cuvette according to claim 1,
   wherein the separating walls allow the cuvette to bend elastically about a vertical axis.

7. A cuvette according to claim 6,
   wherein the separating wall connects parallel positions along at most half of a side face of the cuvette to improve an even temperature distribution.

8. A cuvette according to claim 1,
   wherein the cuvette is made of a material with optical and elastic properties.

9. A cuvette according to claim 1,
   wherein the cuvette is made of first and second materials.

10. A cuvette according to claim 9,
    wherein the materials are mutually different polymers so that the first material has optical properties and the second material has elastic properties.

11. A cuvette according to claim 10,
    wherein the positions are made of the first material and the separating walls or brackets or both are made of the second material.

12. A cuvette according to claim 10,
    wherein the first material is acryl.

13. A cuvette according to claim 10,
    wherein the second material is polyurethane.

* * * * *